United States Patent [19]

Eibofner et al.

[11] Patent Number: 5,512,245
[45] Date of Patent: Apr. 30, 1996

[54] PROCESS FOR THE CLEANING AND/OR DISINFECTION AND PROVIDING MAINTENANCE CARE TO A HOLLOW OR TUBULAR MEDICAL DENTAL TREATMENT INSTRUMENT

[75] Inventors: Eugen Eibofner, Biberach; Bernhard Kuhn, Schemmerhofen, both of Germany

[73] Assignee: Kaltenbach & Voigt GmbH & Co., Biberach, Germany

[21] Appl. No.: 277,239

[22] Filed: Jul. 19, 1994

[30] Foreign Application Priority Data

Jul. 26, 1993 [DE] Germany ............. 43 25 046.7

[51] Int. Cl.$^6$ ................ A61L 2/16; B08B 9/00
[52] U.S. Cl. ............ 422/28; 422/14; 134/168 C; 433/104
[58] Field of Search ............... 422/7, 14, 28; 433/104; 134/168 C, 166 R, 169 C, 102.2

[56] References Cited

U.S. PATENT DOCUMENTS

| | | | |
|---|---|---|---|
| 2,669,242 | 2/1954 | Wightman | 134/166 R |
| 3,811,408 | 5/1974 | Thompson | 134/166 C |
| 4,294,797 | 10/1981 | Eibofner | 422/36 |
| 4,544,355 | 10/1985 | Eibofner et al. | 433/104 |
| 4,752,444 | 6/1988 | Bowen et al. | 422/28 |
| 5,165,503 | 11/1992 | Hoffman | 433/104 |
| 5,197,499 | 3/1993 | Bodenmiller et al. | 134/95.2 |
| 5,308,579 | 5/1994 | Melon et al. | 433/104 |
| 5,318,443 | 6/1994 | Overmyer | 433/104 |
| 5,326,492 | 7/1994 | Hodam, Jr. | 252/106 |

FOREIGN PATENT DOCUMENTS

| | | |
|---|---|---|
| 4125223A1 | 2/1992 | Germany . |
| 42 35 699.7 | 4/1994 | Germany . |

*Primary Examiner*—Robert J. Warden
*Assistant Examiner*—Theresa T. Snider
*Attorney, Agent, or Firm*—Scully, Scott, Murphy & Presser

[57] ABSTRACT

A process for the cleaning and/or disinfection and maintenance care of an, in particular, hollow or tubular medical treatment instrument, in particular a medical or dental treatment instrument, such as a handpiece, in which the treatment instrument is cleaned and/or disinfected with a preferably liquid cleaning and/or disinfecting agent and is then subjected to maintenance care with a maintenance care agent, is characterized in that there is used a cleaning agent and/or a disinfecting agent and/or a maintenance care agent, one or more of which agents contains or contain a medium which ensures mixing of the cleaning and/or disinfecting agent with the maintenance care agent.

9 Claims, No Drawings

PROCESS FOR THE CLEANING AND/OR DISINFECTION AND PROVIDING MAINTENANCE CARE TO A HOLLOW OR TUBULAR MEDICAL DENTAL TREATMENT INSTRUMENT

BACKGROUND OF THE INVENTION

1. Field of the Invention

The invention relates to a process for cleaning and/or disinfecting, and lubricating, hollow or tubular medical treatment instruments.

2. Description of the Prior Art

For the treatment of the human or animal body various forms of treatment instruments are used by means of which body fluids are removed or treatment media delivered, as is the case e.g. with a medical or dental handpiece for the treatment of the body. Such a handpiece may be a treatment instrument for mechanical or other treatment of the body, such as e.g. a drilling or milling handpiece, an injection handpiece or a probe.

In all the cases mentioned above, cleaning and/or disinfection of the handpiece is needed after the treatment, in order to remove fouling or contamination of the handpiece.

Cleaning and/or disinfection is difficult with hollow treatment instruments, because the cleaning, disinfection and maintenance care must also take place in small crevices and gaps of the hollow space of the treatment instrument, on the one hand in order to avoid a fouling or contamination of the next body to be treated and on the other hand to ensure a complete internal maintenance care of the treatment instrument, which is of substantial significance for the operating life and functionality of the treatment instrument.

In DE-A-40 24 171 A1 there is described a process for the maintenance care of medical and dental instruments in which the instruments are cleaned by being blown out and are disinfected by being boiled in a water bath. Thereafter, internal drying of the instruments is effected by blowing out with hot air. By such a treatment, a lubricating agent between mechanically cooperating parts in the instrument is removed. In order to ensure the working of the mechanically cooperating parts of the instrument, oil is blown into the instrument by means of hot air, after the internal drying. By means of a subsequent blowing out of the instrument with hot air, the lubrication is intensified and, moreover, excess oil is removed from the hollow space of the instrument. Any oil which reaches the exterior of the instrument can thereafter be removed by cleaning with a tenside supplement, in the sense of an external cleaning.

A comparable process for the maintenance care of medical and/or dental instruments is described in DE 41 25 223 A1.

In various treatment instruments several hollow spaces or cavities are present, which serve for different purposes. For example in a medical or dental treatment instrument there are cavities for accommodating drive parts, such as a drive shaft or possibly a transmission unit, and for the passage of media, in particular treatment media such a air, water or spray.

In the applicant's prior patent application P 42 35 699.7 there is described a device and a process for the cleaning and/or disinfection and/or maintenance care of medical or dental handpieces. With this device, the treatment of the instrument or instruments is effected in the water bath of a washing container to which washing water can be supplied, held at a particular level and discharged, by means of a supply and discharge line. In the washing container, there are arranged holders for holding the treatment instruments in upright position. Thereby, two supply lines are associated with each holder which upon placement of the treatment instrument in the associated holder, e.g. by insertion in or on a support, are connected with the various above-described cavities in the treatment instrument. Upon cleaning and/or disinfection the treatment instrument is first cleaned externally and internally in a hot water bath, and possibly also disinfected—which may be effected by the heat or by a disinfectant supplied to the water. The internal cleaning is promoted by blowing out the treatment instrument with preferably hot air, whereby a drying of the cavities may also take place. With this device and process, the maintenance care agent is delivered only to the cavity of the treatment instrument which contains parts which mechanically cooperate with one another which should lubricated and provided with maintenance care. For this purpose, a maintenance care agent, preferably oil, can be blown in via the associated supply line, in particular by means of hot air. Refilling of at least this cavity with washing water can be prevented by the supply of compressed air through the associated supply line, which builds up pressure in the hollow chamber and thereby prevents the spontaneous entry of washing water into this cavity.

With all the above-described processes for maintenance care there is a difficulty in that the cavity or cavities in the treatment instrument to be cleaned and/or disinfected and subjected to maintenance care can be of difficult shapes and can also have narrow crevices, channels and slits, as is particularly the case when drive or bearing parts are arranged and mounted in the cavity, such as e.g. a drive shaft with roller bearings or possibly also a transmission unit with toothed wheels. In such a case it is difficult and time consuming, after cleaning and/or disinfecting with the relevant liquid, then to remove this liquid from the cavity, because small agglomerations of liquid, surface wettings or drops can collect in particular in corners and crevices and channels or between drive or bearing elements which are connected to one another. When thereafter the maintenance care agent is supplied, it cannot reach locations wetted with or occupied by the cleaning or disinfecting liquid. The consequence is inadequate maintenance care, which leads to premature corrosion and wear of the treatment instrument.

The object of the invention is to so further develop a process of the kind described in the introduction that reliable maintenance care is achieved.

SUMMARY OF THE INVENTION

This object is achieved by the inclusion of a medium in at least one of the cleaning/disinfecting/lubricating agents which ensures the mixing of same.

DETAILED DESCRIPTION OF THE PREFERRED EMBODIMENT

In a process in accordance with the invention a cleaning and/or disinfecting fluid and/or a maintenance care agent is used which contains or contain a medium which ensures mixing of the cleaning and/or disinfecting liquid with the maintenance care agent. This medium can be e.g. a solvent or an emulsifier which reduces the surface tension and thereby leads to the desired mixing. As a result of the mixing, maintenance care is achieved also at locations at which the walls of the treatment instrument are wetted by the cleaning and/or disinfecting liquid or to which drops of that liquid adhere.

The advantage which can be achieved by the invention is based not only on the above-described ensuring of maintenance care but also on the fact that the effort required for removing the cleaning and/or disinfecting liquid from the treatment instrument can be reduced and thus the maintenance care can be carried out more quickly and reliably. It is for example possible to do without drying after the cleaning and/or disinfecting, since surfaces which are wetted or occupied by drops are reliably subjected to maintenance care with the process according to the invention.

The invention is not restricted to hollow or tubular treatment instruments. The problem addressed by the invention is present also at external surfaces of the treatment instrument, particularly when the treatment instrument has external slits or constrictions at which the cleaning and/or disinfecting liquid can readily adhere.

A lubricating oil or dental oil, usual in the present field, is very suitable as maintenance care agent. The maintenance care agent in accordance with the invention may, however, also be a maintenance spray.

Trials have shown that an acceptable mixing is already achieved when the medium is included in a mixture of about 0.5% to 15%, in particular 1% to 10%, preferably 4% or 5% to 8%.

Further, it has been found that an ethoxylated olein is well suited as emulsifier.

The medium or emulsifier in accordance with the invention may be a combination of fatty amine polyglycol and ethoxylated olein or an ethoxylated polyalkylene glycolether in particular in the above-mentioned weight percent ranges. Thereby it has further been found that in the first case a weight percent proportion of about 4% and in the second case of about 8% is well suited. Moreover, with these emulsifiers, biodegradability is ensured.

The process according to the invention is suitable both for manual and machine cleaning and/or disinfecting and maintenance care of the treatment instrument, e.g. in that the internal cleaning and/or internal disinfecting can be effected by washing through or blowing through of the cleaning and/or disinfecting liquid, or in that the cleaning and/or disinfecting is effected in a cleaning and/or disinfecting bath, as described in the introduction. The present invention in advantageous in particular in combination with the processes discussed in the introduction.

The process according to the invention can be advantageously carried out both when the medium according to the invention is contained in the maintenance care agent and when it is contained in the cleaning and/or disinfecting agent, because the relevant mixture can be made available or ready mixed in a container. Since the quantity of the necessary maintenance care agent is small, it is recommended to mix the medium in the maintenance care agent. If the cleaning and/or disinfecting liquid is water, it is advantageous and more simple to take it from a normal water supply.

We claim:

1. A process for cleaning and/or disinfecting and providing maintenance care to a hollow or tubular medical treatment instrument, comprising:

subjecting the treatment instrument to a cleaning and/or disinfecting with a liquid cleaning or disinfecting agent; and subsequently subjecting the treatment instrument to a maintenance care agent;

wherein at least one of said agents includes a medium which enables mixing of the cleaning and/or disinfecting agent with said maintenance care agent on at least one interior surface of said treatment instrument, during said maintenance care step.

2. The process set forth in claim 1, wherein the medium is a solvent.

3. The process set forth in claim 1, wherein the medium is an emulsifier.

4. The process set forth in claim 1, wherein the maintenance care agent comprises an oil.

5. The process set forth in claim 1, wherein the step of subjecting the treatment instrument to a maintenance care agent comprises applying the maintenance care agent as a spray.

6. The process set forth in claim 1, wherein the medium comprises 1% to 10% of the agent which contains said medium.

7. The process set forth in claim 1, wherein the medium comprises an ethoxylated olein.

8. The process set forth in claim 1, wherein the step of subjecting the treatment instrument to the maintenance care comprises blowing the maintenance care agent into the instrument.

9. The process set forth in claim 1, wherein the process is carried out in a washing container which includes a quantity of cleaning and/or disinfecting agent therein, whereby the step of subjecting the treatment instrument to cleaning and/or disinfecting comprises inserting the instrument into the quantity of cleaning and/or disinfecting agent.

* * * * *